United States Patent
Kwak et al.

(10) Patent No.: US 7,295,325 B2
(45) Date of Patent: Nov. 13, 2007

(54) TIME-RESOLVED MEASUREMENT TECHNIQUE USING RADIATION PULSES

(75) Inventors: Hidong Kwak, San Jose, CA (US); Gary Janik, Palo Alto, CA (US); Mehrdad Nikoonahad, Menlo Park, CA (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 336 days.

(21) Appl. No.: 10/672,725

(22) Filed: Sep. 26, 2003
(Under 37 CFR 1.47)

(65) Prior Publication Data
US 2004/0207850 A1    Oct. 21, 2004

Related U.S. Application Data

(60) Provisional application No. 60/416,850, filed on Oct. 8, 2002.

(51) Int. Cl.
*G01B 9/02* (2006.01)
(52) U.S. Cl. ........................ 356/502; 356/432
(58) Field of Classification Search ............. 356/35.5, 356/432, 502, 28.8; 250/227.19, 227.27
See application file for complete search history.

(56) References Cited

U.S. PATENT DOCUMENTS

| | | | |
|---|---|---|---|
| 4,526,465 A * | 7/1985 | Corti et al. ................. | 356/35.5 |
| 4,710,030 A | 12/1987 | Tauc et al. | |
| 5,909,279 A * | 6/1999 | Pepper et al. ............... | 356/479 |
| 6,108,087 A | 8/2000 | Nikoonahad et al. | |
| 2001/0046052 A1* | 11/2001 | Toida ......................... | 356/480 |

* cited by examiner

*Primary Examiner*—Hwa (Andrew) Lee
(74) *Attorney, Agent, or Firm*—Davis Wright Tremaine LLP

(57) ABSTRACT

In one embodiment, a probe pulse is first stretched into a pulse of longer duration. The probe pulse comprises a plurality of wavelength components in a bandwidth, so that each temporal portion of the converted pulse corresponds to and comprises one of the wavelength components. This converted pulse is supplied to the sample at the time when it is affected by the disturbance of the sample caused by a pump pulse. Changes in characteristics of the sample at the wavelength components of the temporal portions of the converted pulse are then detected after the converted pulse has been modified by the sample. Such changes are then analyzed to derive characteristics of the sample. In another embodiment, a converter passes to a detector radiation from a probe beam that has been modified by the sample during a temporal sequence of time intervals, where the time intervals correspond to displacement in a spatial record. The radiation passed comprises radiation from the probe beam when it is affected by the disturbance in the sample caused by a pump pulse. The output of the detector is then analyzed to determine the characteristics of the sample.

91 Claims, 7 Drawing Sheets

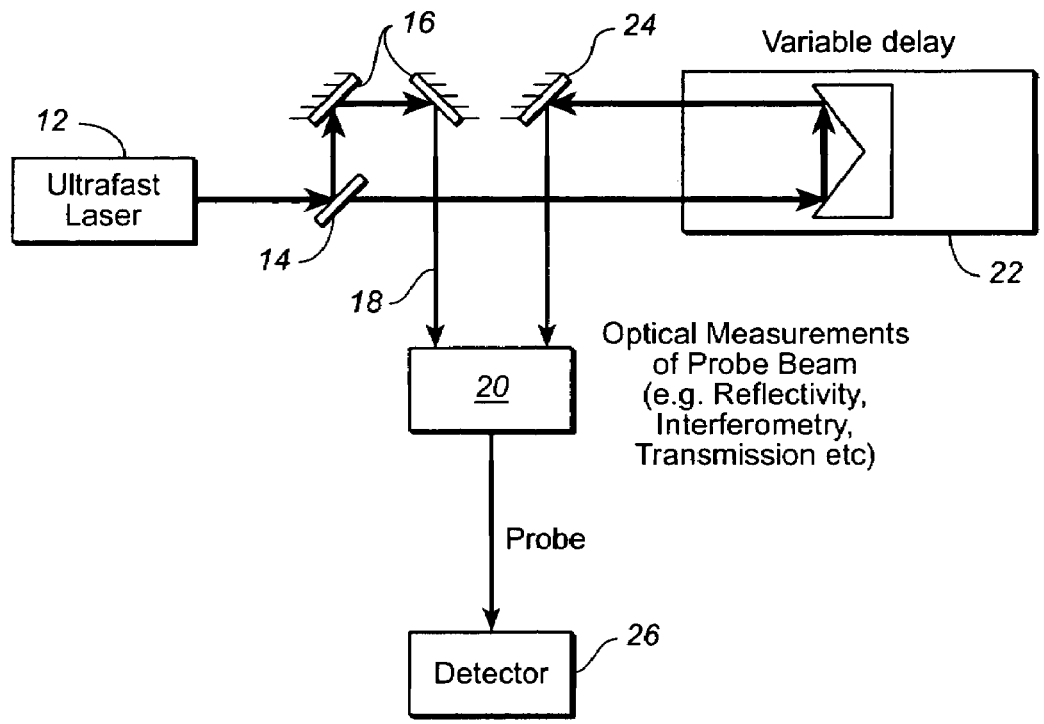
FIG._1 (PRIOR ART)
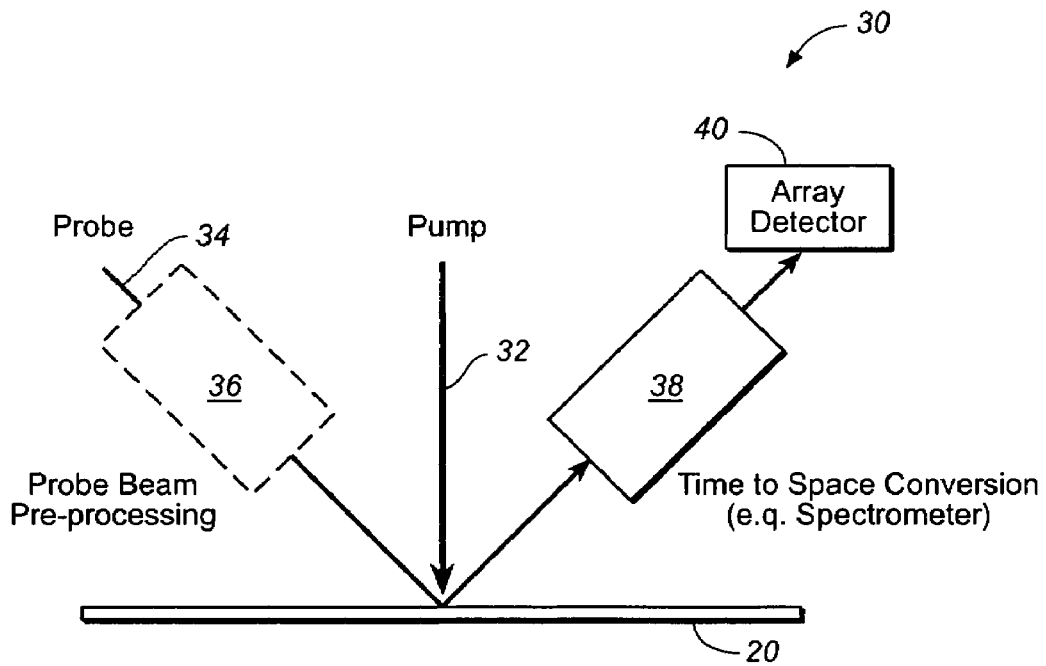
FIG._2

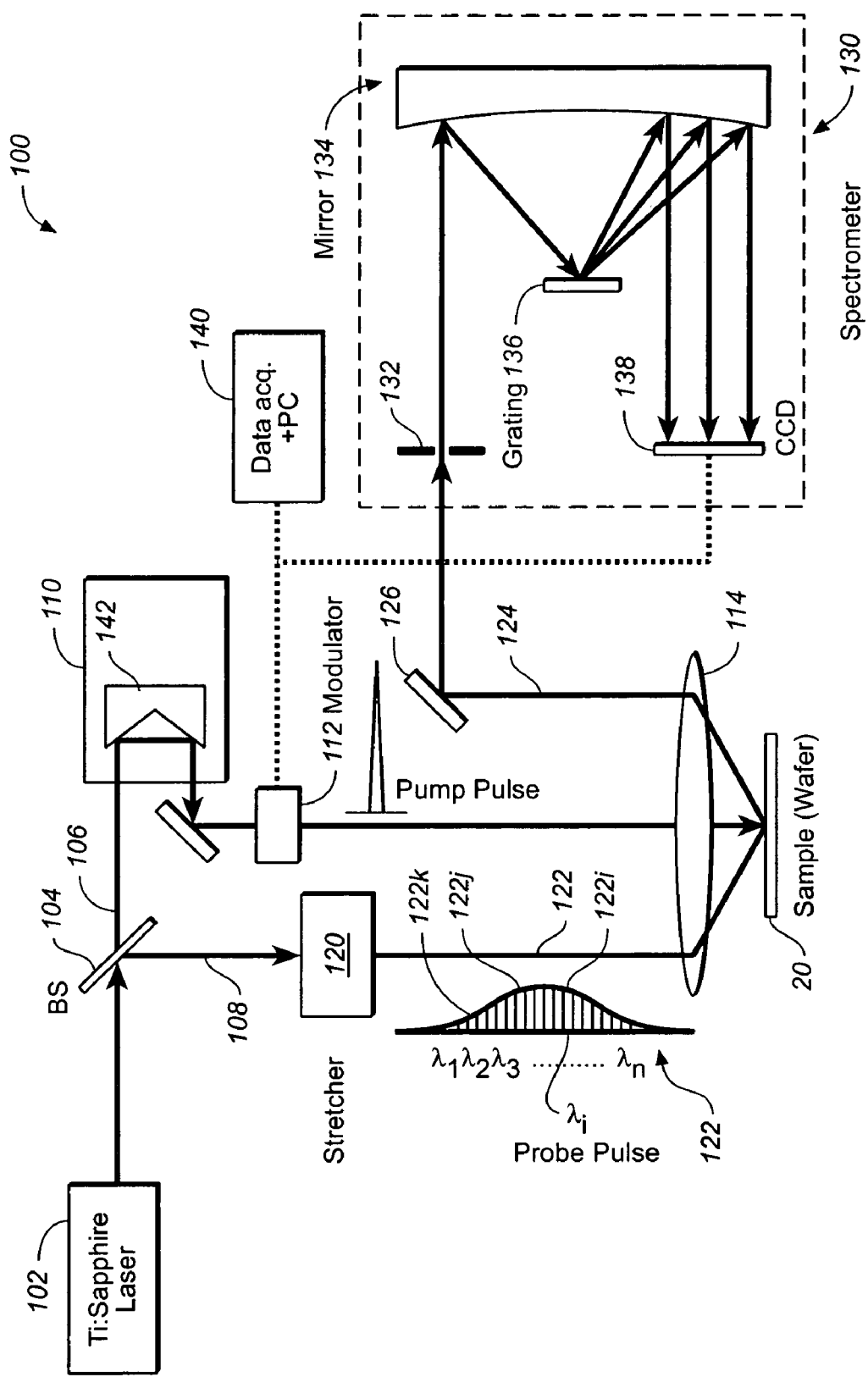
FIG._3

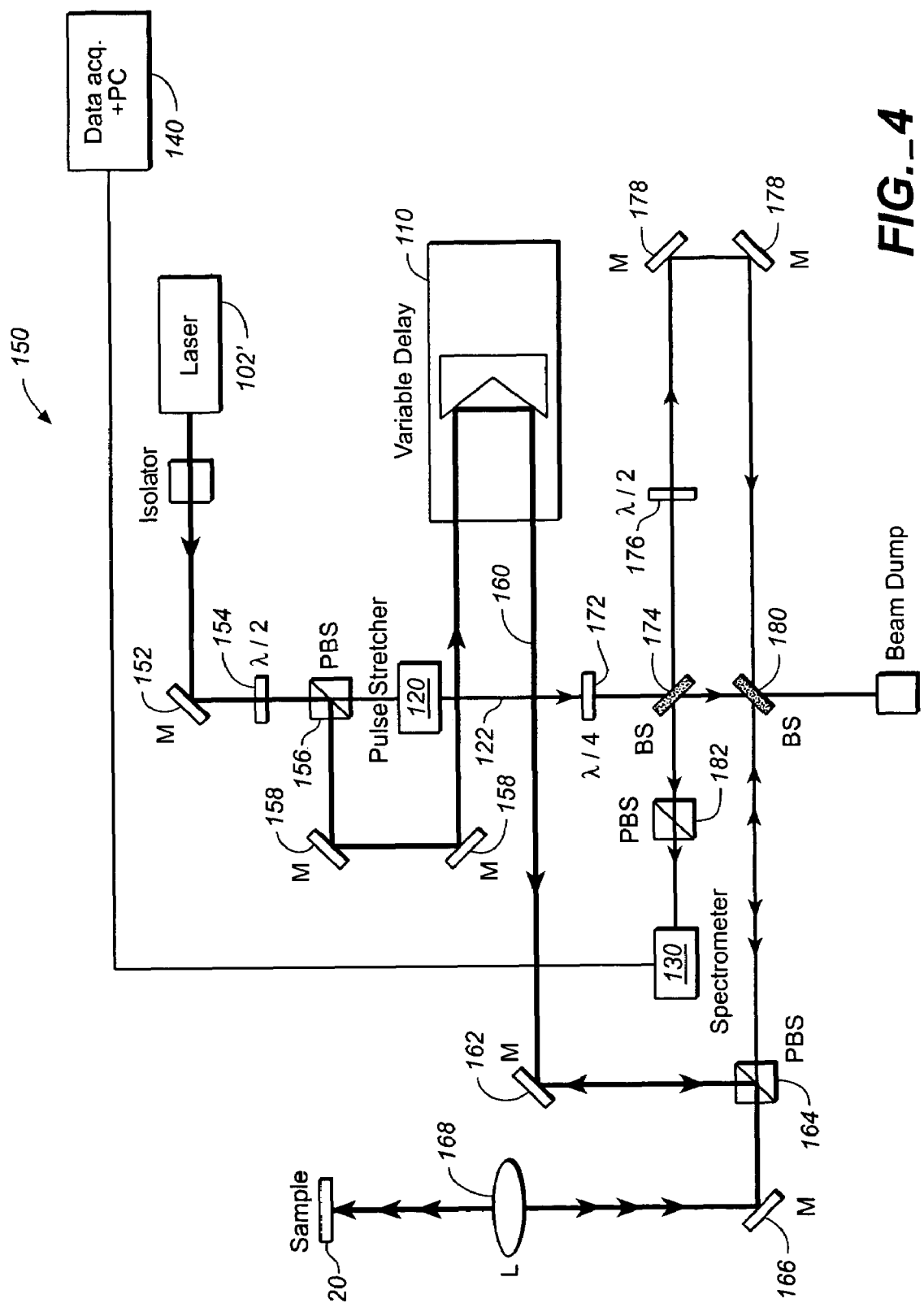
FIG._4

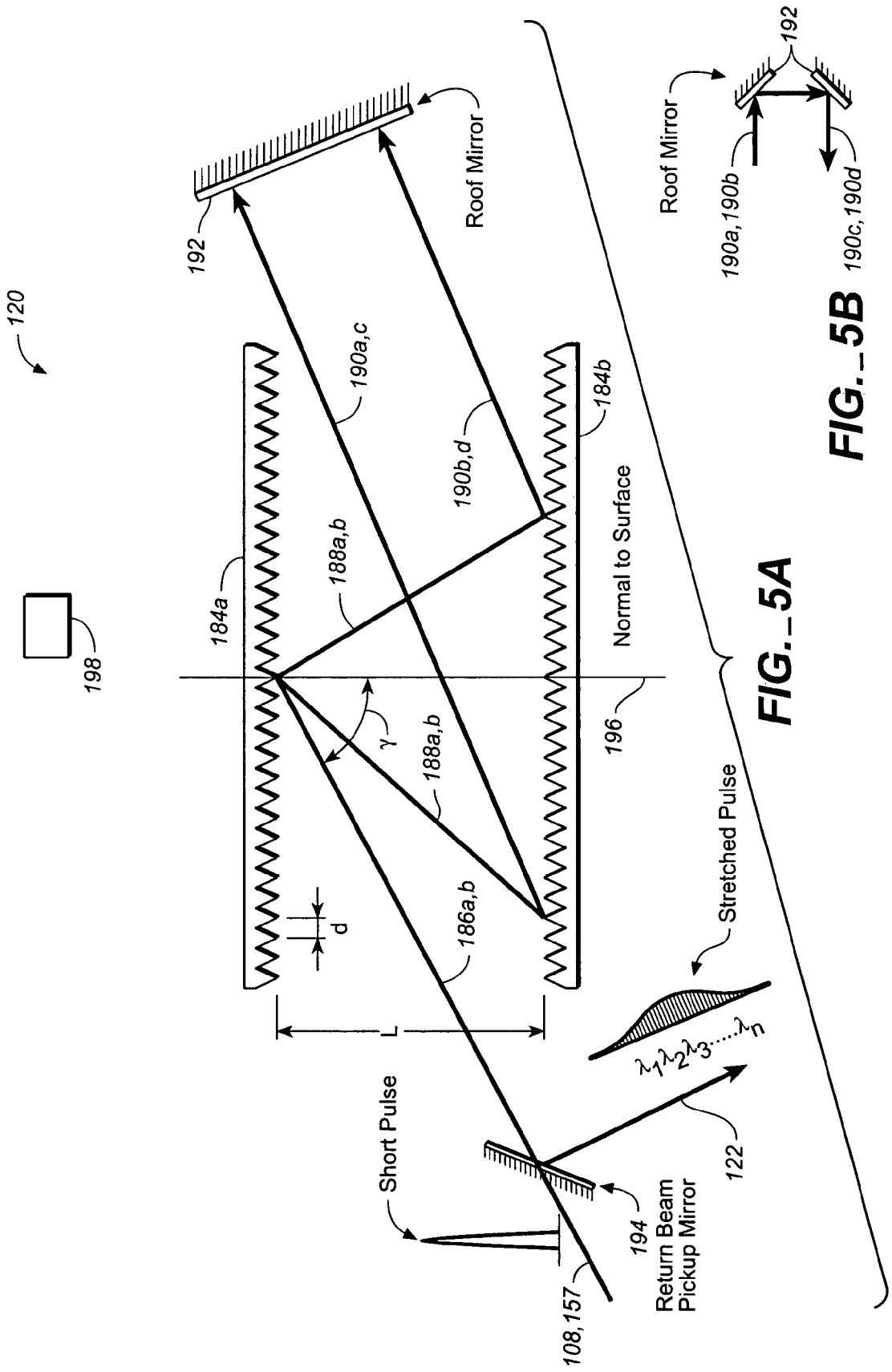
FIG._5A
FIG._5B

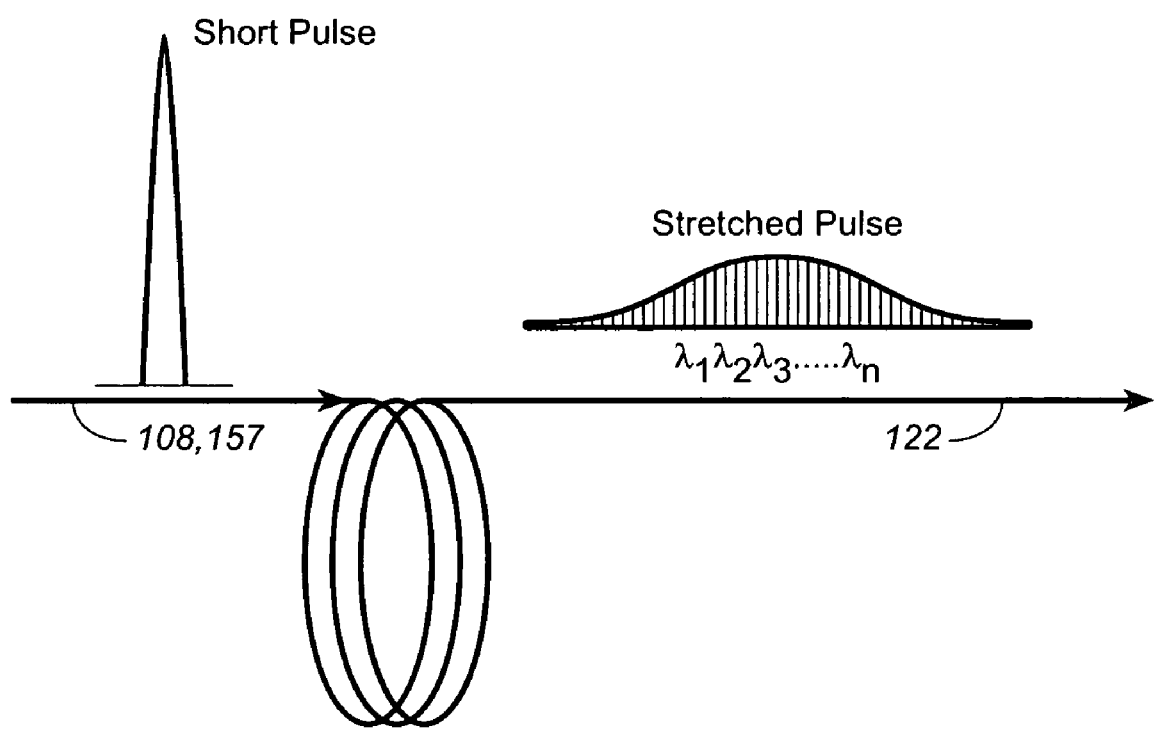
FIG._5C

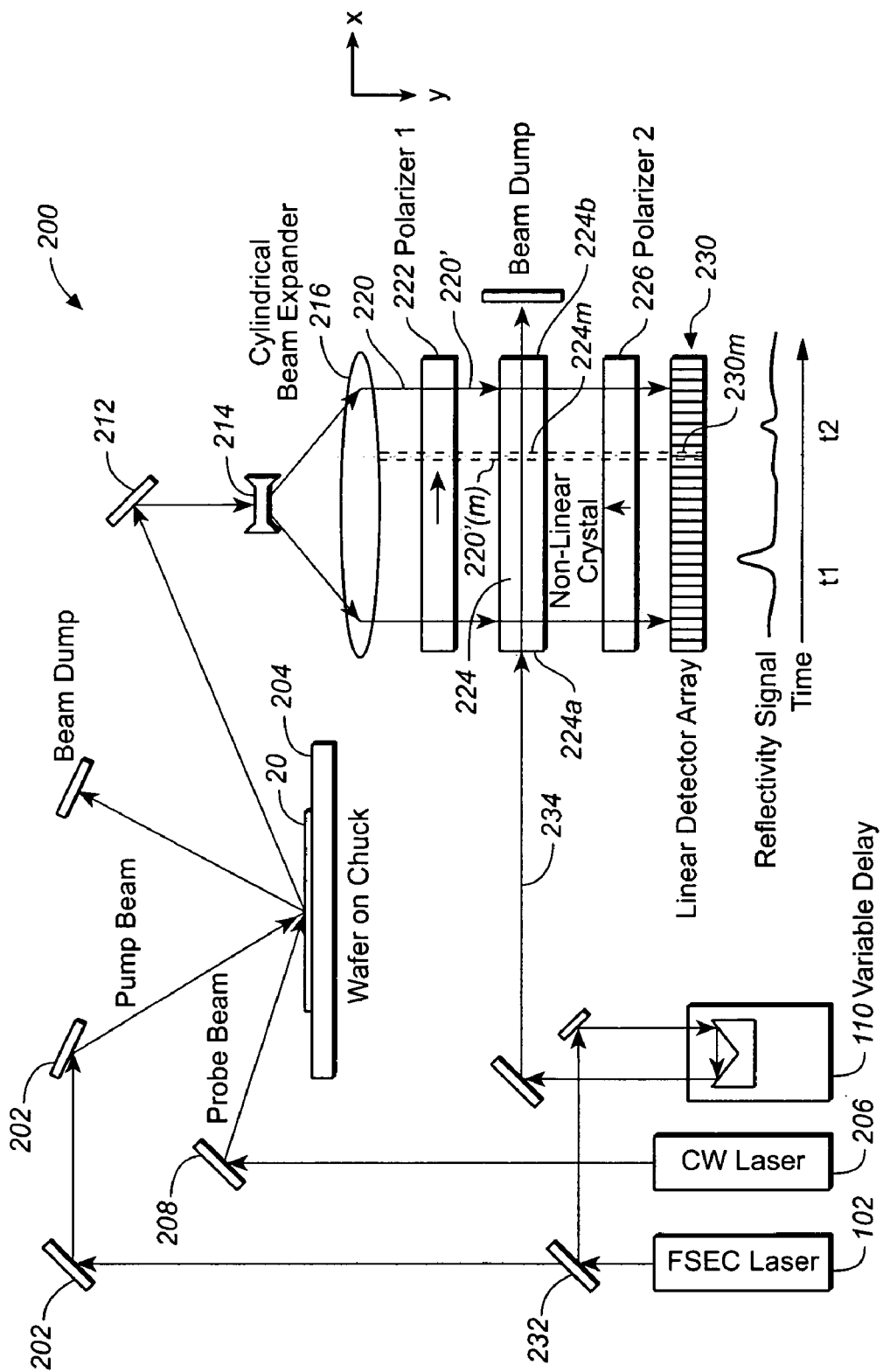
FIG._6

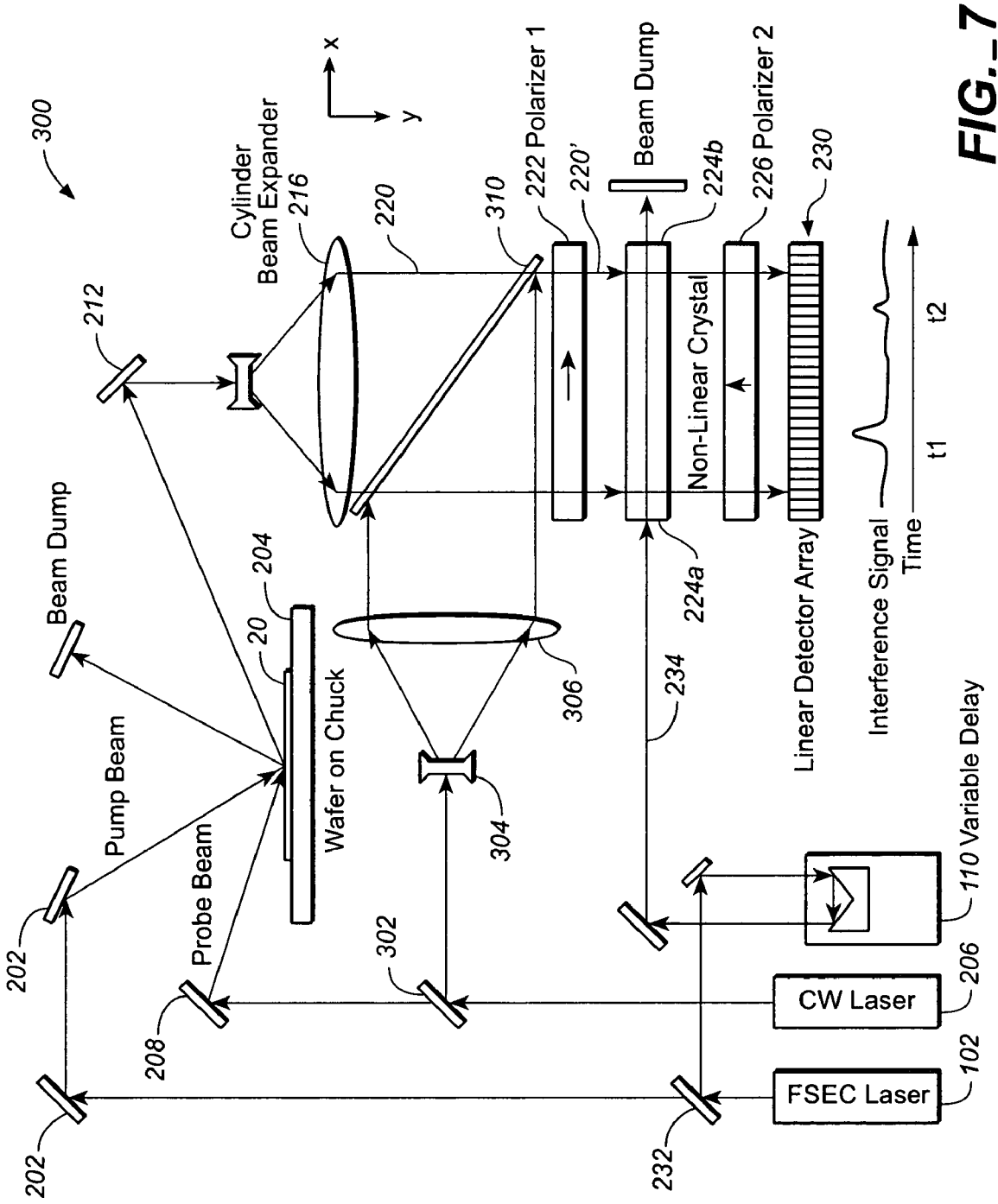

TIME-RESOLVED MEASUREMENT TECHNIQUE USING RADIATION PULSES

This application claims the benefit of U.S. Provisional Patent Application No. 60/416,850 filed on Oct. 8, 2002 which application is incorporated by reference herein in its entirety.

BACKGROUND OF THE INVENTION

This invention relates in general to the measurement of characteristics of a sample and in particular to a time-resolved measurement technique that excites a sample by means of a pump beam and then measures the sample characteristics by means of a probe beam.

Ellipsometry and reflectometry are powerful techniques for film thickness measurement in semiconductor processing. In cases where the film under examination is transparent to the illuminating radiation, ellipsometry for example can measure films down to one monolayer thick (3-10 Angstroms). However, both ellipsometry and reflectometry fail in cases where the film under examination is opaque. Metallic films, which play a major role in integrated circuit fabrication, fall into this category. Optical radiation is absorbed within the first few tens to hundreds of Angstroms of the film, depending on the wavelength. For example, using green radiation at a wavelength of 0.5 micron in aluminum, the absorption length is less than 83 Angstroms. At longer wavelengths, and in particular at infra red wavelengths, this situation gets better, but still ellipsometry cannot provide the full solution with reference to metallic films or other optically opaque films.

Time resolved pulse-echo ultrasound is a well known technique for thickness measurement in situations where the thickness of interest is a few millimeters or at least tens of microns. For films used in semiconductor processing, one needs extremely short pulses so that the surface echoes from subsurface film interfaces can be time resolved. Such pulses can be generated by ultrashort laser pulses and the general area of this art is known as picosecond photoacoustics. The physical processes involved are as follows: a short laser pulse is absorbed within one absorption length from the surface, causing a rise in local temperature of the surface. Through the temperature coefficient of expansion (expansivity) the film undergoes thermal stresses leading to a pulse, such as an elastic or acoustic pulse, which propagates across the film at the speed of sound. Given the velocity of sound in the film, if one measures the time of flight across the film, one can compute the film thickness. The key-remaining issue, is therefore, the detection of the acoustic disturbance once it bounces back from the rear side of the film and reaches the front surface.

A number of approaches have been proposed for measuring the thicknesses of films using the above-described time resolved pulse-echo technique. One approach is described in U.S. Pat. No. 6,108,087 assigned to the assignee of the present application. In this technique, a pump pulse is directed to the top surface of a film in a sample to generate an acoustic pulse. The acoustic pulse propagates downwards until it reaches an interface between the bottom surface of the film in the sample and the substrate or an other film and is reflected back to the top surface of the film as a first echo. A reflection of the first echo propagates downwards and is again reflected back towards the surface as the second echo. Interferometry is used to detect a displacement at the surface due to the arrival of the acoustic pulse, thereby leading to a measurement of the time lapse between the first and second echoes which, in turn, leads to the computation of the film thickness.

Another approach is described in U.S. Pat. No. 4,710,030. This patent states that once a stress pulse is reflected from the rear side of the film and reaches the surface, it changes the optical constants of the surface. The change in the optical constants of the surface leads to a change in reflectivity which is detected by monitoring the intensity of the reflection of a probe beam which also illuminates the surface.

In the approaches described above, however, the probe beams are measured at different time delays by means of a high resolution delay stage that is placed in the path of the pump beam or the probe beam. This delay stage requires that a roof mirror is mechanically translated in order to vary the relative timing relationship between the pump and probe beams so that the change in reflectivity or displacement of the surface of the sample can be measured at different relative time delays between the two beams in order to detect the echoes of the acoustic pulse caused by the pump pulse. In other words, after each measurement in which a sequence of pump pulses and the probe beam are applied to measure the reflectivity or displacement, the delay stage increases or decreases the relative delay between the pump and probe beams, and a next measurement is then taken. This is repeated until adequate data points have been acquired for identifying the times at which the first and the second echoes are detected. The time delay between the first and second echoes may then be used for determining film thickness. In order for adequate data points to be acquired, the above procedure requires a significant amount of time for repeating the measurements at different relative delays between the pump and probe beams.

It is therefore desirable to provide an improved technique for measuring film thickness(es) that are faster than the above-described approaches.

SUMMARY OF THE INVENTION his invention is based on the observation that, by means of a conversion process by which the different relative delay times between the pump and probe pulses or beams can be converted or transformed into a different parameter such as a wavelength record or a spatial record, then the above-described need to repeat the measurements at different relative delays between the pump and probe beams may be eliminated and the various echoes of the acoustic pulse may be detected in the same measurement process without having to change the relative timing relationship between the pump and probe pulses or beams. Preferably the different echoes of the acoustic pulse can be detected within a time period that is much (e.g. at least one order of magnitude) shorter than the time required in the approaches above.

In one embodiment, the probe pulse is first converted into a chirped pulse of longer duration than the duration of the probe pulse prior to the conversion. The probe pulse comprises a plurality of wavelength components in a bandwidth, so that each temporal portion of the converted pulse corresponds to and comprises one of the wavelength components. This converted pulse is supplied to the sample at the time when it is affected by the disturbance of the sample caused by the pump pulse. Changes in characteristics of the sample modify the wavelength components of the temporal portions of the converted pulse. These temporal portions are then detected after the converted pulse has been modified by the sample preferably in the same measurement without having to alter a timing relation between the pump and probe pulses. Such changes are then analyzed to derive characteristics of the sample.

In another embodiment, a converter passes to a detector radiation from a probe beam that has been modified by the sample during a temporal sequence of time intervals, where the time intervals correspond to displacement in a spatial record. The radiation passed comprises radiation from the probe beam when it is affected by the disturbance in the sample caused by a pump pulse. The output of the detector is then analyzed to determine the characteristics of the sample.

BRIEF DESCRIPTION OF THE DRAWINGS

FIG. 1 is a schematic view of an optical measurement system illustrating a conventional method.

FIG. 2 is a schematic view of a system for measuring a sample by means of a pump beam and a probe beam to illustrate an aspect the invention.

FIG. 3 is a schematic view of an optical measurement system for measuring change in reflectivity of a sample caused by a pump beam to illustrate one embodiment of the invention.

FIG. 4 is a schematic view of an interferometric optical system for measuring change in elevation of a sample caused by a pump beam to illustrate another embodiment of the invention.

FIG. 5a is a schematic view of a grating pulse stretcher useful in the embodiments of FIGS. 3 and 4.

FIG. 5b is a schematic view of the roof mirror of FIG. 5a.

FIG. 5c is a schematic view of an optical fiber pulse stretcher useful in the embodiments of FIGS. 3 and 4.

FIG. 6 is a schematic view of an optical system for measuring change in reflectivity of a sample caused by a pump beam to illustrate another embodiment of the invention.

FIG. 7 is a schematic view of an interferometric optical system for measuring change in displacement of a surface of a sample caused by a pump beam to illustrate yet another embodiment of the invention.

For simplicity in description, identical components are identified by the same numerals in this application.

DETAILED DESCRIPTION OF THE EMBODIMENTS

FIG. 1 is a schematic view of an optical system for measuring changes in characteristics of a sample caused by a pump pulse to illustrate a conventional approach. As shown in FIG. 1, system 10 includes a laser 12 which provides short radiation pulses to a beam splitter 14. A portion of each pulse is diverted by the beam splitter 14 and reflected by mirrors 16 as a pump pulse which is directed to a sample 20. The pump pulse 18 causes a change in temperature at the exposed top surface of a first film at the top portion of the sample, causing an acoustic pulse to be generated which travels away from the surface of the film towards an interface between the film and a substrate or a second film of the sample. The acoustic pulse is reflected by the interface back towards the exposed surface of the film whereupon the acoustic pulse is again reflected back towards the interface and again back towards the surface as a second echo. A portion of each pulse provided by the laser passes the beam splitter 14 towards a variable delay 22, reflected by mirror 24 towards the surface of the film at or close to the area of the surface affected by the pump pulse. The variable delay 22 introduces a time delay between the time when the pump pulse reaches the sample and the time the probe pulse reaches the sample. The change in reflectivity, transmission or surface displacement is detected by detector 26. The amount of relative delay between the pump and probe pulses is varied so that the output of the detector may be plotted against the time delay, such as in a graphical plot shown in FIG. 5 in U.S. Pat. No. 6,108,087. From such a graphical plot, the first and second echoes may be identified, so that the thickness of the film can be calculated if the speed of sound within the film is known.

From the above description, however, it is evident that a large number of measurements are required so that the graphical plot described above can be constructed. For each of the data points in such plot, the above-described measurement has to be performed. After each data point has been obtained, the variable delay 22 alters the relative delay between the pump and probe pulses and the above-described measurement repeated to obtain another data point in the plot. This process has to be repeated so that an adequate number of data points are obtained in order to be able to identify the echoes from the interface between the film and the substrate. This process is therefore very time-consuming.

FIG. 2 is a schematic view of an optical system for measuring characteristics of the sample by means of a pump pulse and a probe beam to illustrate an aspect of the invention. As shown in FIG. 2, a pump pulse 32 is applied to the surface of a sample 20. A probe beam 34 is applied to the area of the surface of sample 20 affected by the pump pulse 32. In some embodiments, the probe beam 34 may undergo pre-processing by pre-processing optics 36 before the probe beam is applied to the sample. Radiation from the probe beam that has been modified by the sample is then converted by converter 38 in a manner so that the different relative timing relationship between the arrival times of the probe beam and the pump pulse at the surface of the sample 20 is converted into a record of another parameter. In other words, the record of this other parameter corresponds to the relative time delay between the pump and probe beams. The record of the parameter covers the relative time delays between the pump and probe beams when they are affected by a change in sample characteristics caused by the pump beam. Such parameter record is then detected by means of an array detector 40. In this manner, characteristics of the sample 20 can be measured during a single measurement without having to alter the timing relationship between the pump and probe beams as in conventional approaches.

FIG. 3 is a schematic view of an optical system for measuring characteristics of a sample by detecting the change in reflectivity of the surface of the sample caused by a pump pulse to illustrate one embodiment of the invention. As shown in FIG. 3, a Ti:sapphire laser 102 provides a stream of ultra-fast radiation pulses. Preferably, the durations of these pulses are less than one picosecond, and more preferably, less than 0.1 picosecond. In one embodiment, for example, laser 102 provides pulses having durations of the order of femtoseconds such as 15 femtoseconds. With such duration, the radiation pulses have a relatively broad spectrum such as 16 nanometers or greater. These pulses are divided into two streams by a beam splitter 104: a stream of pump pulses 106 and a stream of pulses 108. The pump pulses 106 pass through an optical path including an optical delay 110 used for calibrating the instrument 100 in the manner described below.

After being modulated by modulator 112, the pump pulse is focused by an objective 114 to the surface of a sample 20 such as that of a semiconductor wafer. Where one or more films are present at the surface of the wafer, the pump pulse will be absorbed by the exposed surface of the top first film. The heat that results from the absorption causes thermal stress in the film and causes an acoustic pulse to be generated which propagates downwards to reach an interface between the film and the substrate of the wafer or the surface of another film. The acoustic pulse is then reflected at the interface back towards the top surface of the first film as the first echo. When the first echo reaches the top exposed surface of the first film, it changes the optical constants at the surface, thereby altering its reflectivity. The first echo is reflected by the top surface of the first film back towards the interface where it is again reflected back towards the first surface as the second echo which also changes the reflectivity of the surface of the first film. This process continues with subsequent echoes until the energy of the acoustic pulse is dissipated. Such changes in reflectivity can be measured by means of the probe pulses.

As described above, the pump pulse train from the laser is modulated by modulator 112 at a low frequency of several kHz to tens of kHz. Therefore, the echoes at the surface would also include wavelength components at this low frequency. This low frequency component in the probe beam is then detected as described below to enhance the accuracy of measurement.

The probe pulses 108 are supplied to a pulse stretcher 120 which converts each of the pulses 108 of very short durations to a chirped one that has a duration long enough to cover a time window for measuring the change in surface reflectivity of the sample caused by the different echoes of the acoustic pulse generated by the pump pulse. In one embodiment, the pulse stretcher 120 converts each of the pulses 108 to a probe pulse that has the duration not less than about 10 picoseconds. The converted chirped probe pulse 122 of longer duration is illustrated graphically alongside the optical path of such pulse. As shown in the graphical representation, the converted chirped pulse 122 includes a number of temporal portions such as 122$i$ for the $i^{th}$ temporal portion of the pulse.

The pulse stretcher 120 is such that different wavelength components in the ultra-fast pulses 108 are delayed by different amounts relative to the arrival time of the pump pulse at the sample so that each temporal component contains one of the wavelength components of the pulses 108 prior to the conversion. For example, temporal component 122$i$ may contain the wavelength component $\lambda_i$ in the pulses 108. In this manner, there would be a one-to-one correspondence between a temporal portion of the converted pulse 122 and one of the wavelength components in the pulses 108 prior to conversion. Time resolution of each pixel in the array detector is determined by detection spectral bandwidth of the pixel in an array detector. To have a certain time resolution dt at each pixel in the array detector, at least detection spectral bandwidth of dw=4/dt is required. However, there would be an average time delay of each temporal portion relative to the arrival time of the pump pulse at the sample corresponding to an average wavelength value. By detecting the wavelength components the reflection of a converted chirped pulse 122 by the surface of the sample 20, it is therefore possible to correlate these wavelength components with the different temporal portions 122$i$ within the converted pulse. Therefore, if the detection system is calibrated so that the average time delay of each temporal portion such as 122$i$ relative to the pump pulse is known, by detecting the reflection of these different wavelength components, it is possible to determine the arrival times of the different echoes of the acoustic pulse caused by the pump pulse in a single measurement without altering the timing relationship between the pump pulses 106 and the pulses 108.

Thus, the converted chirped probe pulse 122 is focused by objective 114 to an area of the surface of sample 20 that has been affected by the acoustic pulse, such as by the echoes. Reflection of the converted chirped pulse 122 is collimated by objective 114 as beam 124, reflected by mirror 126 to a spectrometer 130. The reflection 124 of the converted chirped pulse 122 passes through a slit 132 and is reflected by mirror 134 to a grating 136 which causes the different wavelength components in the reflected radiation 124 to be diffracted at different angles. These different wavelength components are collected by mirror 134 and reflected towards an array detector such as a charged couple device (CCD) 138 for detecting the different wavelength components. The output of the CCD 138 is supplied to a data acquisition unit and computer block 140 for processing. Modulator 112 supplies to the block 140 the low frequency reference at which the pump pulses 106 are modulated. The reflection 124 of the converted chirped pulse 122 also contains components at this low modulation frequency reference. Processing block 140 then processes the components in the output of the CCD 138 at such modulating frequency for improved signal-to-noise ratio.

Prior to performing any actual measurements on samples, the above-described detection portion of the system 100 is first calibrated by means of variable delay 110. Thus, by moving the optical block 142 by means of a motor (not shown), the optical path length of the pump pulses 106 can be increased or decreased, thereby decreasing or increasing the time delay between the pulses 108 and the pump pulses 106. Since the converted chirped probe pulses 122 are intended to detect the echoes of the acoustic pulse caused by the pump pulse, the probe pulses are typically supplied at a certain time delay after the arrival times of the pump pulses at the surface of sample 20. Therefore, the calibration is done in terms of the time delay of the temporal portions (e.g. 122$i$) of the converted pulse 122 relative to the pump pulse.

To provide a reference for the time delays between the pump and probe pulses, the calibration procedure is carried out so that such timing relationship can be measured from the output of the detector. By introducing different amounts of relative delay between the converted pulse 122 and pump pulse 106 by means of variable delay 110, it is then possible to determine the delay time for each of at least some of the spectral component in the converted chirped probe pulses 122. The zero time delay can be determined by applying the pump pulse and then determining the wavelength at which the reflectivity of the surface of the sample has changed due to ultrafast transient response. When a pump pulse 106 reaches the surface of the sample, it causes a large change in reflectivity of the sample surface, as shown at time 0 in FIG. 5 of U.S. Pat. No. 6,108,087. One (122$i$) of the temporal portions 122 would therefore be affected by this change in reflectivity, and this change is detected by spectrometer 130 detecting a particular wavelength component and marks the time of arrival of the pump pulse. The reading from the variable delay 110 then is the zero delay stage position for such temporal component 122$i$. The delay introduced by delay 110 is then altered to detect the zero delay stage position of another temporal component in the converted chirped probe pulses 122. This process is repeated so that the zero delay stage positions of temporal components that would cover the time frame of interest (i.e. cover the relative time delays between the pump and probe pulses where the echoes reach the surface of the sample) have been determined. The delay stage is calibrated with very high precision. Therefore, if all the zero delay stage positions for spectral components have been found, the relative delay time for each of the spectral components in a subsequent measurement can be determined since the relative path differences between the spectral components are known. The above-described calibration process is preferably carried out using a reference sample which has a high transient reflectivity change at zero time delay.

While the different wavelength components in the corresponding temporal portions of the converted pulse 122 are detected at slightly different times, they are detected within the time duration of the converted pulse, which is preferably of the order of picoseconds. Therefore, compared to the time required to mechanically move a delay stage in order to change the timing relationship between the pump and probe pulses as in conventional approaches described above, and for all practical purposes, these wavelength components are detected substantially simultaneously. Thus, the characteristics of the sample can be measured without having to alter the timing relationship between the pump and probe pulses as required in conventional approaches.

In the embodiment of FIG. 3, sample characteristics such as film thicknesses are measured by detecting the change in reflectivity. Alternatively, the film thickness parameter can be measured by detecting the displacement at the surface of the sample caused by echoes of the acoustic pulse as described in U.S. Pat. No. 6,108,087. In other words, when an echo of the acoustic pulse reaches the exposed surface of the top film, it displaces a small portion of the surface.

FIG. 4 is a schematic view of an interferometric optical system for measuring sample characteristics such as film thickness by detecting the displacement of the surface of the sample. Laser 102' (which may be similar to laser 102 of FIG. 3) supplies linearly polarized light pulses that are reflected by mirror 152 towards a halfwave plate 154. Plate 154 rotates the plane of polarization of the laser beam pulses, with the result that the S-polarization components of the rotated beam pulses are reflected by polarizing beam splitter 156 as the pump beam 160, and P-polarization components are passed by the beam splitter 156 as the reference and probe beam pulses 157 to be used in the interferometer described below. The pump beam is reflected by mirrors 158 towards the variable delay 110. After being delayed by variable delay 110, the pump beam 160 is reflected by mirrors 162 towards a polarizing beam splitter 164. The beam splitter reflects the S-polarized pump beam towards mirror 166 which, in turn, reflects the pump beam through lens 168 to sample 20 to create the acoustic (elastic) pulses or other pulses in the sample.

After being modulated by the pulse stretcher in the same manner as that described above in reference to FIG. 3, the sequence of pulses that passes polarizing beam splitter 156 is passed through pulse stretcher 120 to stretch the pulses in the beam in the manner described above. It then passes a quarter-wave plate 172 which causes the beam to be a circularly polarized beam with a P-polarized component and a S-polarized component with a phase shift $\pi/2$ between the two components. Beam splitter 174 passes a portion of each pulse in the incident beam as a reference pulse and reflects the remainder as a corresponding probe pulse, so that two sequences of reference and probe pulses would emerge. The variable delay 110 adjusts the length of the optical path of the pump pulses 160 so that the reference pulse in the two sequences would arrive before the arrival of the corresponding pump pulse at sample 20, whereas the probe pulse in the two sequences would arrive at sample 20 after the arrival of the corresponding pump pulse. The reference and probe pulses are reflected by sample 20 through lens 168 and are reflected by mirror 166 towards the beam splitter 164.

In the same manner as that described in reference to FIGS. 2, 3A and 3B of U.S. Pat. No. 6,108,087, each pair of reference and probe pulses in the two sequences and their reflections from sample 20 share the same common optical path between beam splitter 182 and the sample 20. In other words, the probe pulse in each pair of reference and probe pulses is reflected by beam splitter 174 and rotated by halfwave plate 176, reflected by mirrors 178 and passed through beam splitter 180 to polarizing beam splitter 164. A certain component of the probe pulse is passed by polarizing beam splitter 164, reflected by mirror 166 towards sample 20 through lens 168. Reflection of the component of the probe pulse by the sample 20 is passed by polarizing beam splitter 164 and reflected by beam splitters 180 and 174 and passed by the polarizing beam splitter 182 to reach the spectrometer 130. The reference pulse in the pair, on the other hand, or a component thereof, would pass first through beam splitters 174 and reflected by beam splitter 180 towards the polarizing beam splitter 164, reflected by mirror 166 through lens 168 to the sample. The reflection of the reference pulse in the pair passes through lens 168, reflected by mirror 166 and passes through polarizing beam splitter 164 and beam splitter 180 to mirrors 178. It is rotated in phase by halfwave plate 176 and passes through beam splitter 174 and polarizing beam splitter 182 to interfere with its corresponding probe pulse at the spectrometer 130.

Spectrometer 130 has been calibrated in the same manner as that described above in reference to FIG. 3 so that, by detecting the wavelength component in the reflection of the converted or stretched chirped probe and reference pulses, it is possible to associate such wavelength component with the corresponding time delay relative to the arrival time of the corresponding pump pulses at the sample. The interference of the reference and probe pulses in the pair would yield information concerning the displacement of the surface of the sample 20 in the same manner as that described in U.S. Pat. No. 6,108,087. Then a graphical plot similar to that in FIG. 5 of U.S. Pat. No. 6,108,087 may be prepared from the output of spectrometer 130 for identifying the echoes. From the time lapse between the echoes, the thickness of the film can be determined if one has knowledge of the speed of sound in the film. U.S. Pat. No. 6,108,087 is incorporated herein by reference in its entirety.

FIG. 5a is a schematic view of a grating structure to illustrate one embodiment of the pulse stretcher 120 of FIGS. 3 and 4. In reference to FIG. 5a, short pulses that are used for probing the sample (as used in FIGS. 3 and 4) may be stretched by a stretcher comprising two gratings 184a and 184b arranged so that they face and are substantially parallel to one another. Preferably, the two gratings have substantially the same pitch d. The short pulses are supplied along optical path 186a and the different wavelength components in such pulses are diffracted by grating 184a in different directions 188a, 188b and substantially all of the directions in between so that lines 188a, 188b mark the extreme edges of the diffracted beam.

The diffracted wavelength components from grating 184a are collected by grating 184b and collimated into a beam whose extreme positions are marked by lines 190a, 190b. Such beam is reflected by a roof mirror 192 which is shown in more detail in FIG. 5b. As illustrated in FIG. 5b, roof mirror 192 comprises two reflecting surfaces so that beam between lines 190a and 190b is reflected into a reflected beam between lines 190c and 190d in a direction parallel to the beam between lines 190a, 190b but is displaced relative to it in a direction pointing into or out of the plane of the paper in FIG. 5a. The reflected beam between lines 190c, 190d is spectrally combined by grating 184b towards grating 184a and is collected along a path 186b which is reflected by pick up mirror 194 to form the converted and stretched pulse such as pulse 122 of FIG. 3. Pulses 108 bypass mirror 194 since they travel along a path 186a that is displaced from the mirror 194 in a direction pointing into or out of the plane of the paper in FIG. 5a. As is evident in FIG. 5a, the different wavelength components in each of the short pulses 108 or 157 experience different optical path lengths along paths exemplified by the extreme portions of the beam at 188a, 188b, 190a, 190b, and along the normal direction 196 to the gratings, so that the different wavelengths are delayed by different amounts, thereby causing these different wavelength components to have a different time delay relative to pump pulses.

Thus, when the distance between the two gratings is L and the angle of incidence of the input short pulses 108 relative to a direction normal to the two gratings is γ, the group velocity dispersion is given by the following:

$$d'' = \frac{d^2\phi}{d\omega^2} = \frac{-\lambda^3 L}{\pi c^2 d^2}\left(1 - \left(\frac{\lambda}{d} - \sin\gamma\right)^2\right)^{-\frac{3}{2}}$$

In the equation above, c is the speed of light and ω is angular frequency of the radiation in the beams 108 and 157. The ratio of the time duration of the stretched and converted chirped pulse 122 relative to the duration of the pulse in the beams 108 and 157 prior to the stretching, or the stretching ratio, is given by:

$$\frac{\tau_{out}}{\tau_{in}} = \sqrt{1 + \frac{\phi''^2}{\tau_{in}} 16(\ln 2)^2}$$

Therefore, where the group velocity dispersion is large, the stretching ratio is approximately proportional to the group velocity dispersion and therefore to the separation L between the gratings. Therefore, if a motor 198 is employed to control the distance L between the two gratings, or the angle of incidence of the input pulse 108 or 157 at grating 184a, the stretching ratio can be controlled. In one embodiment, gratings 184a, 184b each has 120 lines per millimeter. Where the grating separation L is 20 centimeters and the center wavelength of the input pulse 108 or 157 is 800 nanometers, an input pulse having a full width half maximum of 30 femtoseconds can be stretched to a converted output pulse having a full width half maximum of 71 picoseconds in duration.

FIG. 5c is a schematic view of an optical fiber that can also be used as the stretcher 120 in FIGS. 3 and 4. As illustrated schematically, a short input pulse 108 or 157, after passing through the fiber, is converted into a stretched pulse 122.

FIG. 6 is a schematic view of an optical system for measuring sample characteristics by detecting the change in reflectivity of a sample surface that has received pump pulses to illustrate another embodiment of the invention. Instead of using a pulse stretcher for introducing different time delays to wavelength components of an input beam, it is possible to convert different time delays into a spatial record by means of a gating mechanism as is done in the embodiment of FIG. 6. As in the previous embodiments, pump pulses from a laser 102 are supplied, after reflection by mirrors 202 to the wafer 20 supported on a chuck 204. A continuous wave (CW) laser 206 supplies a probe beam which is reflected towards the wafer 20 by mirror 208. Alternatively, instead of a continuous wave (CW) laser, a laser 206 that supply pulses having durations long enough for the measurement can also be used, such as where the pulses have durations not less than about 20 picoseconds.

The reflection of the probe beam is reflected by mirror 212 and expanded by a cylindrical beam expander 214 along the X axis and collimated by lens 216 into a thin sheet of radiation 220 propagating in the Y direction. Beam 220 is passed through a polarizer 222 so that it has a particular polarization. The polarized beam 220' passes through a non-linear crystal 224 into a polarizer 226 which passes only radiation that is substantially orthogonal to the polarization of beam 220'. Therefore, if beam 220' passes through the non-linear crystal 224 with its polarization unaltered, the entire beam 220' will be blocked by the polarizer 226, and no radiation from beam 220' will reach the linear detector array 230. However, if any portion of the non-linear crystal alters the polarization state of a portion of the beam 220', such portion of the beam would have a component that will pass through polarizer 226 to reach the detector array 230.

A portion of each of the pump pulses is diverted by a beam splitter 232 and is delayed by a variable delay 110 to become a gating pulse along optical path 234 applied to one end 224a of a non-linear crystal 224. The non-linear crystal 224 is elongated with its length aligned generally along the X axis. When the gating pulse along optical path 234 is applied to one end of the crystal 224, the pulse propagates from one end 224a of the crystal towards the other end 224b. As the gating pulse reaches a portion of the non-linear crystal along its way to end 224b, it alters the birefringence of the crystal. Such change in birefringence causes the polarization state of a portion of the beam 220' to be altered so that such portion of 220' that reaches the portion of the crystal has a component that is passed by polarizer 226 to reach the detector array 230. Hence, beam 220' may be divided into a number of portions aligned along the X axis, such as portion 220'(m) shown in dotted lines in FIG. 6. The resolution of the spatial portions in the crystal is determined by the pump pulse length. When each of such portions of the beam reaches the non-linear crystal 224, depending upon whether a gating pulse is altering the birefringence of the portion of the crystal receiving such portion of the beam, a fraction of the beam may be passed to a corresponding detector in the detector array 230.

Thus, for example, a portion 220'(m) will reach portion 224m of the crystal. If the gating pulse along path 234 reaches portion 224m, a fraction of the portion 220'(m) of beam 220' will pass through polarizer 226 to reach detector 230m in detector array 230. However, if a gating pulse along path 234 has not reached or has gone past portion 224m of the crystal, then the portion 220'(m) of the beam 220' will be blocked by polarizer 226 so that no radiation will reach detector 230m of the array 230.

Depending upon the relative optical path length difference between the path of the pump pulse from beam splitter 232 to wafer 20 and the path of the gating pulse from beam splitter 232 to end 224a of crystal 224, there is a fixed timing relationship between the gating pulse and the pump pulse. Thus, the gating pulse supplied by path 234 acts as a gating mechanism with a predetermined and fixed timing relationship to the arrival of the pump pulse at the sample. The gating pulse travels along the length of the crystal 224

"opening a gate" to pass a portion of beam 220' along the way. In this manner, the gating mechanism translates a delay time relative to the arrival of the pump pulse at the sample to a spatial relationship or record along the length of the crystal 224 generally in the X direction. By detecting how far along the length of the crystal 224 radiation from beam 220' is detected, the relative time delays between the detection of changes in reflectivity of the sample surface and the time of the arrival of the pump pulse at the sample can be determined.

Therefore, by adjusting the optical path of the gating pulse by means of variable delay 110, it is possible to select the timing of the gating pulse along path 234 provided to the crystal 224 so that beam 220' contains radiation that has been affected by the acoustic pulse in wafer 20 caused by the pump pulse, including different echoes of the acoustic pulse in the wafer. If the index of refraction of the crystal 224 of the gating pulse is known, then the speed of propagation of the gating pulse through the crystal is also known. Then the time delay between successive echoes of the acoustic pulse can be calculated from the speed of propagation of the gating pulse through the crystal and the spatial record of the echoes.

The above-described function of the gating pulse along optical path 234 therefore operates to pass a portion of radiation from the probe beam at a predetermined timing relationship relative to the arrival of the pump pulse at the sample 20 so that the distance along the X direction of the linear array 230 reflects the relative time delay of portions of beam 220' that have been affected by the acoustic pulse and its echoes. Thus, as shown in FIG. 6, for example, at time t1, a significant change in reflectivity of the sample surface is observed. At time t2, another significant change in reflectivity (although less than that of time t1) is observed. Where the optical path length of the gating pulse is adjusted so that at time t1 the reflectivity is caused by an echo and that of time t2 is caused by the immediately following echo, for example, then the time difference t1–t2 can be used to derive film thickness in wafer 20, if the speed of sound in the film is known. Obviously, the time window selected corresponding to the length of crystal 224 and length of linear detector array 230 can be chosen to record also more than two echoes as well as the change in reflectivity caused by the pump pulse itself; such and other variations are within the scope of the invention.

FIG. 7 is a schematic view of another optical instrument illustrating yet another embodiment of the invention. Instrument 300 is similar to instrument 200, with the exception that a portion of the laser beam from laser 206 is diverted by beam splitter 302 and expanded by a cylindrical beam expander 304 and collimated by lens 306 and reflected by beam splitter 310 to interfere with beam 220' at detector 230, in order to detect the displacement of the sample surface caused by the pump beam. Except for such difference, the embodiment 300 operates in the same manner as instrument 200.

While in some of the embodiments above, the probe beam is directed to the area influenced by the pump pulses to detect the radiation reflected by the area to determine times of arrival of echoes, it is also possible to direct the probe beam towards a different area of the sample to detect change in reflectivity or surface displacement caused by the acoustic pulse after it is transmitted through the sample or film in a transmission detection scheme. Such and other variations are within the scope of the invention.

While the invention has been described above by reference to various embodiments, it will be understood that changes and modifications may be made without departing from the scope of the invention, which is to be defined only by the appended claims and their equivalent. All references referred to herein are incorporated by reference in their entirities.

What is claimed is:

1. An apparatus for measuring characteristics of a sample, comprising:
   a first source supplying a pump pulse of radiation to a first surface area of the sample to cause a disturbance of the sample at the first surface area;
   a second source supplying a radiation probe pulse having a duration of less than about 1 picosecond for probing the sample at the first surface area, the probe pulse having a plurality of wavelength components in a bandwidth;
   a converter converting the probe pulse into a corresponding converted pulse of longer duration than duration of the probe pulse prior to conversion so that each temporal portion of the converted pulse corresponds to and comprises one of the wavelength components, and supplying the converted pulse to the sample at the first surface area;
   a detector detecting changes in characteristics of the sample at wavelengths of the wavelength components corresponding to temporal portions of the converted pulse after the converted pulse has been modified by the sample and providing an output, wherein at least some of the temporal portions have been affected by the disturbance; and
   a device analyzing the output of the detector or a signal derived therefrom to determine characteristics of the sample.

2. The apparatus of claim 1, wherein said disturbance causes a pulse to propagate in the sample, said converted pulse having a duration long enough for measuring propagation of the pulse in the sample.

3. The apparatus of claim 2, wherein said disturbance causes a pulse to propagate in the sample, said device analyzing changes in characteristics of the sample at different delay times of the portions relative to the arrival time of the pump pulse at the first surface area of the sample to determine characteristics of the sample.

4. The apparatus of claim 2, wherein said converted pulse has a duration not less than about 10 picoseconds.

5. The apparatus of claim 1, said detector detecting changes in characteristics of the sample at different delay times of the portions relative to the arrival time of the pump pulse at the first surface area of the sample by detecting changes in characteristics of the first surface area.

6. The apparatus of claim 5, said detector detecting changes in characteristics of the sample at different delay times of the portions relative to the arrival time of the pump pulse at the first surface area of the sample by detecting changes in optical characteristics of the first surface area.

7. The apparatus of claim 6, said detector detecting changes in characteristics of the sample at different delay times of the portions relative to the arrival time of the pump pulse at the first surface area of the sample by detecting changes in optical reflectivity of the first surface area.

8. The apparatus of claim 5, said detector detecting changes in characteristics of the sample at different delay times of the portions relative to the arrival time of the pump pulse at the first surface area of the sample by detecting changes in elevation of the first surface area.

9. The apparatus of claim 8, said detector comprising an interferometer detecting changes in elevation of the first surface area.

10. The apparatus of claim 1, said probe pulse having wavelength components across a substantially continuous spectrum in the bandwidth.

11. The apparatus of claim 1, said probe pulse having a duration of less than about 0.1 picosecond.

12. The apparatus of claim 1, said converter comprising a pulse stretcher.

13. The apparatus of claim 12, said pulse stretcher comprising a pair of gratings or an optical fiber.

14. The apparatus of claim 13, said pulse stretcher comprising the pair of gratings and an instrument capable of adjusting a distance between the pair of gratings, or an angle of incidence of the probe pulse to the pair of gratings.

15. The apparatus of claim 1, said detector comprising a spectrometer.

16. The apparatus of claim 15, said device analyzing output of the spectrometer to derive changes in characteristics of the sample at different delay times of the temporal portions of the converted pulse relative to the arrival time of the pump pulse at the first surface area of the sample.

17. The apparatus of claim 16, wherein said disturbance causes an elastic pulse to propagate in the sample, said device analyzing changes in characteristics of the sample at different delay times of the portions relative to the arrival time of the pump pulse at the first surface area of the sample to determine characteristics of the sample.

18. The apparatus of claim 17, said sample having interfaces therein, wherein the elastic pulse propagates between the interfaces, causing echoes in the sample, said device analyzing changes in characteristics of the sample at different delay times of the temporal portions relative to the arrival time of the pump pulse at the first surface area of the sample to determine at least one distance between two interfaces of the sample.

19. The apparatus of claim 1, the second source providing a pair of a probe pulse and a reference pulse of radiation so that the probe pulse is directed to said first surface area when said first surface area is moved by the pump pulse and the reference pulse to a second surface area so that the pair is modified by the sample, said apparatus further comprising optics directing reflections of the pair of pulses from the sample to the detector so that the modified pair of pulses interfere at the detector to provide the output.

20. The apparatus of claim 19, wherein the probe pulse together with the modified probe pulse substantially share a common optical path with the reference pulse together with the modified reference pulse between the second source and the detector.

21. The apparatus of claim 1, further comprising a delay element that alters a timing relationship between the pump pulse and the converted probe pulse to calibrate the apparatus so that wavelength components detected by the detector and delay times of the temporal portions relative to the arrival time of the pump pulse at the first surface area of the sample are correlated.

22. The apparatus of claim 1, wherein said first source supplies radiation for the pump or probe pulse, and wherein the second source comprises optics that diverts a portion of the radiation supplied by the first source to supply the probe or pump pulse.

23. An apparatus for measuring characteristics of a sample, comprising:
a first source supplying a pump pulse of radiation to the sample to cause a disturbance of the sample;
a second source supplying a radiation probe pulse having a duration of less than about 1 picosecond for probing the sample, the probe pulse having a plurality of wavelength components in a bandwidth;
a converter converting the probe pulse into a corresponding converted pulse of longer duration than the probe pulse so that each temporal portion of the converted pulse at a particular time corresponds to and comprises one of the wavelength components, and supplying the converted pulse to the sample;
a detector detecting the wavelength components of the temporal portions of the converted pulse after the converted pulse has been modified by the sample and providing an output, wherein at least some of the temporal portions have been affected by the disturbance; and
a device analyzing the output of the detector or a signal derived therefrom to determine said characteristics of the sample.

24. An apparatus for measuring characteristics of a sample, comprising:
a first source supplying a pump pulse of radiation to a first surface area of the sample to cause a disturbance of the sample at the first surface area;
a second source supplying to the sample a probe beam of radiation for probing the sample at the first surface area;
a detector detecting in a detection path radiation from the probe beam after the probe beam has been modified by the sample;
a converter in the detection path so that the converter passes to the detector radiation from the modified probe beam during time intervals in a temporal sequence, where the time intervals in the sequence correspond to displacement in a spatial record, wherein the time intervals during which radiation is passed by the converter have a predetermined timing relationship with arrival of the pump pulse at the first surface area of the sample; and
a device analyzing an output of the detector to determine said characteristics of the sample.

25. The apparatus of claim 24, wherein the converter converts into the spatial record the time intervals during which radiation from the probe beam is passed to the detector, and the device analyzes the detector output in accordance to the spatial record.

26. The apparatus of claim 24, wherein the converter comprises an optical gate having a gating mechanism that is controlled by the pump pulse.

27. The apparatus of claim 26, wherein the optical gate comprises a non-linear crystal.

28. The apparatus of claim 27, said converter providing a gating pulse having the predetermined timing relationship with the arrival of the pump pulse at the first surface area of the sample, said gating pulse propagating along a first direction in the crystal, causing a portion of the modified probe beam to be passed through a portion of the crystal along a second direction transverse to the first direction when the gating pulse reaches such portion of the crystal, wherein the detector comprises an array of detecting units arranged alongside the crystal, each detecting unit in the array detecting the modified probe beam after passing a portion of the crystal adjacent to such unit.

29. The apparatus of claim 28, wherein the array of detecting units arranged alongside the crystal in a third direction substantially parallel to the first direction, so that location of each unit along the third direction corresponds to a time interval during which radiation from the probe beam is passed to the detector.

30. The apparatus of claim 29, wherein the device analyzes outputs of the detecting units in reference to their locations along the third direction.

31. The apparatus of claim 28, wherein the gating pulse alters locally a birefringence of the non-linear crystal.

32. The apparatus of claim 24, the second source supplying to the sample a substantially continuous wave probe beam of radiation.

33. The apparatus of claim 24, wherein the time intervals together extend over a time window, wherein the duration of the window is not less than about 20 picoseconds.

34. The apparatus of claim 24, the second source supplying to the sample a pulsed probe beam of radiation, with a pulse duration that is not less than about 20 picoseconds.

35. The apparatus of claim 24, further comprising a beam expander that expands radiation modified by the sample in a first direction before conversion by the converter into a beam having an elongated cross-section in the first direction.

36. The apparatus of claim 35, wherein the expanded beam comprises portions aligned in the first direction, said converter passing portions of the expanded beam in response to a gating pulse having the predetermined timing relationship with the arrival of the pump pulse at the first surface area of the sample.

37. The apparatus of claim 36, wherein the detector comprises a detector array comprising detecting units aligned in a direction substantially parallel to the first direction, each unit detecting a portion of the modified probe beam after passing the converter.

38. The apparatus of claim 36, wherein the converter comprises a gating mechanism that passes portions of the expanded beam in response to arrival of the gating pulse.

39. The apparatus of claim 38, wherein the converter comprises a crystal and wherein the gating pulse propagates through the crystal along a direction substantially parallel to the first direction.

40. The apparatus of claim 39, wherein the gating pulse alters locally a birefringence of the crystal.

41. The apparatus of claim 24, wherein the time intervals precede and follow a time corresponding to arrival time of the pump pulse at the first surface area.

42. The apparatus of claim 24, wherein the time intervals together extend over a time window, and wherein duration of the window is not less than about 20 picoseconds.

43. The apparatus of claim 24, said detector detecting changes in characteristics of the sample at different times at which radiation from the probe beam is passed to the detector by detecting changes in characteristics of the first surface area.

44. The apparatus of claim 43, wherein the converter converts into a spatial record along a first direction the times at which radiation from the probe beam is passed to the detector, said detector comprising an array of detecting units arranged along a direction substantially parallel to the first direction.

45. The apparatus of claim 44, said detector detecting changes in optical characteristics of the first surface area caused by the pump pulse.

46. The apparatus of claim 45, said detector detecting changes in optical reflectivity of the first surface area.

47. The apparatus of claim 45, said detector detecting changes in elevation of the first surface area.

48. The apparatus of claim 47, said detector comprising an interferometer detecting changes in elevation of the first surface area.

49. The apparatus of claim 47, said interferometer interfering radiation from the probe beam modified by the sample with radiation from the probe beam that is not modified by the sample.

50. The apparatus of claim 24, said probe beam being substantially monochromatic.

51. The apparatus of claim 24, the second source providing a reference beam that is substantially coherent with the probe beam, wherein the modified probe beam and the reference beam interfere at the detector to provide the output.

52. A method for measuring characteristics of a sample, comprising:

supplying a pump pulse of radiation to a first surface area of the sample to cause a disturbance of the sample at the first surface area;

supplying a radiation probe pulse having a duration of less than about 1 picosecond for probing the sample at the first surface area, the probe pulse having a plurality of wavelength components in a bandwidth;

converting the probe pulse into a corresponding converted pulse of longer duration than duration of the probe pulse prior to conversion so that each temporal portion of the converted pulse corresponds to and comprises one of the wavelength components, and supplying the converted pulse to the sample at the first surface area; and detecting the wavelength components corresponding to temporal portions of the converted pulse after the converted pulse has been modified by the sample and providing an output, wherein at least some of the temporal portions have been affected by the disturbance.

53. The method of claim 52, wherein said disturbance causes a pulse to propagate in the sample, said converted pulse having a duration long enough for measuring propagation of the pulse in the sample.

54. The method of claim 53, wherein said converted pulse has a duration not less than about 10 picoseconds.

55. The method of claim 52, said probe pulse having wavelength components across a substantially continuous spectrum in the bandwidth.

56. The method of claim 52, said probe pulse having a duration of less than about 0.1 picosecond.

57. The method of claim 52, said converting comprising stretching the probe pulse.

58. The method of claim 57, said pulse stretching comprising providing a pair of gratings or an optical fiber, and adjusting a distance between the pair of gratings, or an angle of incidence of the probe pulse to the pair of gratings.

59. The method of claim 52, said detecting comprising dividing radiation from the sample into its wavelength components.

60. The method of claim 52, wherein a pair of a probe pulse and a reference pulse of radiation are provided so that the probe pulse is directed to said first surface area when said first surface area is moved by the pump pulse and the reference pulse to a second surface area so that the pair is modified by the sample, said method further comprising directing reflections of the pair of pulses from the sample to the detector so that the modified pair of pulses interfere at the detector to provide the output.

61. The method of claim 60, wherein the probe pulse together with the modified probe pulse substantially share a common optical path with the reference pulse together with the modified reference pulse.

62. The method of claim 52, further comprising altering a timing relationship between the pump pulse and the converted probe pulse to calibrate a system for carrying out the method so that wavelength components detected by the detector and delay times of the temporal portions relative to the arrival time of the pump pulse at the first surface area of the sample are correlated.

63. The method of claim 52, wherein said supplying comprises diverting a portion of the radiation supplied for the pump or probe pulse to supply the probe or pump pulse.

64. A method for measuring characteristics of a sample, comprising:
supplying a pump pulse of radiation to the sample to cause a disturbance of the sample;
supplying a radiation probe pulse having a duration of less than about 1 picosecond for probing the sample, the probe pulse having a plurality of wavelength components in a bandwidth;
converting the probe pulse into a corresponding converted pulse of longer duration than the probe pulse so that each temporal portion of the converted pulse corresponds to and comprises one of the wavelength components, and supplying the converted pulse to the sample; and
detecting the wavelength components of the temporal portions of the converted pulse after the converted pulse has been modified by the sample and providing an output, wherein at least some of the temporal portions have been affected by the disturbance.

65. A method for measuring characteristics of a sample, comprising:
supplying a pump pulse of radiation to a first surface area of the sample to cause a disturbance of the sample at the first surface area;
supplying to the sample a probe beam of radiation for probing the sample at the first surface area;
detecting by means of a detector in a detection path radiation from the probe beam after the probe beam has been modified by the sample; and
passing to the detector radiation from the modified probe beam during time intervals in a temporal sequence of time intervals, where the time intervals in the sequence correspond to displacement in a spatial record, wherein the time intervals during which radiation is passed by the converter have a predetermined timing relationship with arrival of the pump pulse at the first surface area of the sample.

66. The method of claim 65, wherein the converting employs a gating mechanism that provides a gating pulse having the fixed timing relation ship with the pump pulse.

67. The method of claim 66, wherein the gating mechanism employs a non-linear crystal, said gating pulse propagating along a first direction in the crystal, causing a portion of the modified probe beam to be passed through a portion of the crystal along a second direction transverse to the first direction when the gating pulse reaches such portion of the crystal, wherein the detector comprises an array of detecting units arranged alongside the crystal, each detecting unit in the array detecting the modified probe beam after passing a portion of the crystal adjacent to such unit.

68. The method of claim 67, wherein the gating pulse alters locally a birefringence of the non-linear crystal.

69. The method of claim 65, wherein the time intervals together extend over a time window, wherein the duration of the window is not less than about 20 picoseconds.

70. The method of claim 65, wherein the probe beam of radiation comprises pulses with a pulse duration that is not less than about 20 picoseconds.

71. The method of claim 65, further comprising expanding radiation modified by the sample in a first direction before the conversion into a beam having an elongated cross section in the first direction.

72. The method of claim 71, wherein the expanded beam comprises portions aligned in the first direction, wherein said converting passes portions of the expanded beam in response to a gating pulse having the predetermined timing relationship with the arrival of the pump pulse at the first surface area of the sample.

73. The method of claim 72, wherein the detector comprises a detector array comprising detecting units aligned in a direction substantially parallel to the first direction, each unit detecting a portion of the modified probe beam after passing the converter.

74. The method of claim 72, wherein the converting employs a gating mechanism that passes portions of the expanded beam in response to arrival of the gating pulse.

75. The method of claim 74, wherein the converting employs a crystal and wherein the gating pulse propagates through the crystal along a direction substantially parallel to the first direction.

76. The method of claim 75, wherein the gating pulse alters locally a birefringence of the crystal.

77. The method of claim 65, wherein the time intervals precede and follow a time corresponding to arrival time of the pump pulse at the first surface area.

78. The method of claim 65, wherein the time intervals together extend over a time window, and wherein duration of the window is not less than about 20 picoseconds.

79. The method of claim 65, said detector detecting changes in characteristics of the sample at different times at which radiation from the probe beam is passed to the detector for detecting changes in characteristics of the first surface area.

80. The method of claim 79, wherein the converting converts into a spatial record along a first direction the times at which radiation from the probe beam is passed to the detector, said detector comprising an array of detecting units arranged along a direction substantially parallel to the first direction.

81. The method of claim 80, said detecting comprising interfering radiation from the probe beam modified by the sample with radiation from the probe beam that is not modified by the sample.

82. The method of claim 65, said probe beam being substantially monochromatic.

83. The method of claim 65, further comprising providing a reference beam that is substantially coherent with the probe beam, wherein said detecting comprises interfering the modified probe beam and the reference beam at the detector to provide the output.

84. The apparatus of claim 1, wherein said detector provides said output to indicate arrival times of a plurality of echoes of an elastic pulse caused by the disturbance without altering any timing relationship between the pump and probe pulses.

85. The apparatus of claim 1, said detector detecting changes in characteristics of the sample at the wavelength components of the temporal portions of the converted pulse after the converted pulse has been modified by the sample within a time duration not more than the time duration of the converted pulse.

86. The apparatus of claim 24, wherein said converter passes portions of the modified probe beam at different displacements to form the spatial record during said sequence of time intervals, each displacement corresponding to one of the time intervals of the sequence.

87. The apparatus of claim 86, wherein said modified probe beam is in the shape of a thin sheet, and converter passes different portions of the modified probe beam along its elongated cross sectional dimension at different displacements to form the spatial record.

88. The apparatus of claim 87, wherein the converter comprises an optical gate having a gating mechanism that is controlled by the pump pulse for selectively passing different portions of the modified probe beam.

89. The method of claim 52, wherein said providing provides said output to indicate arrival times of a plurality of echoes of an elastic pulse caused by the disturbance without altering any timing relationship between the pump and probe pulses.

90. The method of claim 65, wherein said passing passes portions of the modified probe beam at different displacements to form the spatial record during said sequence of time intervals, each displacement corresponding to one of the time intervals of the sequence.

91. The method of claim 90, wherein said modified probe beam is in the shape of a thin sheet, and said passing passes different portions of the modified probe beam along its elongated cross sectional dimension at different displacements to form the spatial record.

* * * * *